US008263052B1

(12) United States Patent
Marchese et al.

(10) Patent No.: US 8,263,052 B1
(45) Date of Patent: Sep. 11, 2012

(54) TOPICAL DRYING COMPOSITION COMPRISING ENCAPSULATED TREHALOSE AND METHOD OF USING SAME

(76) Inventors: Frank P. Marchese, Bronxville, NY (US); Harold Mermelstein, Bronx, NY (US); Tycho Speaker, Santa Cruz, CA (US)

( * ) Notice: Subject to any disclaimer, the term of this patent is extended or adjusted under 35 U.S.C. 154(b) by 0 days.

(21) Appl. No.: 12/586,371

(22) Filed: Sep. 22, 2009

(51) Int. Cl.
*A61K 8/60* (2006.01)
*A61K 8/06* (2006.01)
*A61K 8/04* (2006.01)
*A61Q 15/00* (2006.01)

(52) U.S. Cl. ............................. 424/65; 514/53; 424/401

(58) Field of Classification Search ........................ None
See application file for complete search history.

(56) References Cited

U.S. PATENT DOCUMENTS

| 4,264,586 | A | * | 4/1981 | Callingham et al. | 424/68 |
| 5,160,732 | A | * | 11/1992 | Katsoulis et al. | 424/68 |
| 5,179,220 | A | * | 1/1993 | Katsoulis et al. | 556/27 |
| 5,705,171 | A | * | 1/1998 | Iovanni et al. | 424/401 |
| 5,911,975 | A | * | 6/1999 | Mendolia et al. | 424/65 |
| 6,403,067 | B1 | * | 6/2002 | Schamper et al. | 424/65 |
| 2001/0031249 | A1 | * | 10/2001 | Oku et al. | 424/65 |
| 2009/0220444 | A1 | * | 9/2009 | Teckenbrock et al. | 424/66 |

OTHER PUBLICATIONS

CAS Registry No. 121-54-0 (Nov. 16, 1984).*
CAS Registry No. 1338-39-2 (Nov. 16, 1984).*
CAS Registry No. 9005-64-5 (Nov. 16, 1984).*
CAS Registry No. 633303-62-5 (Jan. 2, 2004).*

* cited by examiner

*Primary Examiner* — David J Blanchard
*Assistant Examiner* — Peter Anthopolos

(57) ABSTRACT

A topical drying composition is provided for removal of sweat from skin areas which are vulnerable to sweating after sweat producing activities. The drying efficacy of the composition is due to the presence of encapsulated trehalose, with or without aluminum used as aluminum zirconium compound. Application of an effective amount of the composition to the skin prior to exercise or sweat removal activity reduces sweating and accelerates drying of the skin.

17 Claims, No Drawings

TOPICAL DRYING COMPOSITION COMPRISING ENCAPSULATED TREHALOSE AND METHOD OF USING SAME

FIELD OF THE INVENTION

The present invention relates generally to topical drying compositions and is particularly related to topical drying compositions containing an effective amount of encapsulated trehalose. In one aspect, this invention relates to a topical drying composition containing an effective amount of encapsulated trehalose for enhancing drying of the skin when it is applied to the skin of persons, such as athletes, after perspiration due to exercise such as playing tennis, golf, jogging, running, basketball or other sweat-producing aerobic activities. In another aspect, the present invention relates to topical composition containing encapsulated trehalose and known aluminum compounds or aluminum-zirconium compounds.

The invention also relates to a method of using such topical drying compositions.

BACKGROUND OF THE INVENTION

Trehalose is a known non-reducing disaccharide composed of $D_+$glucose units. It is a white, odorless, sweet-tasting powder and, like maltose, is about 45% as sweet as sugar and has a very low hydroscopicity (moisture attraction). Trehalose is found in honey, bread, beer and seafood and there are several prior art patents relating to various uses of trehalose. For example, U.S. Pat. No. 4,839,164 discloses cosmetic compositions containing trehalose which increase the penetration of certain therapeutically beneficial ingredients into the skin thereby enhancing the therapeutic effects of those ingredients on the skin. The trehalose is used in a pharmaceutically acceptable carrier and several trehalose-containing formulations are disclosed in said patent, such as shampoo formulations, hair-conditioning formulations, skin care gel formulations, lotions, and skin care creams.

U.S. Pat. No. 5,543,513 discloses the use of anhydrous trehalose as a desiccant for dehydrating various products such as dehydrated food as well as dehydrated pharmaceuticals. High-quality food products having reduced moisture content can be prepared by incorporating anhydrous trehalose into food products having relatively high moisture content thereby converting the anhydrous trehalose into hydrous crystalline trehalose.

U.S. Pat. No. 6,555,526 discloses an ophthalmic pharmaceutical composition comprising trehalose as the effective ingredient. As disclosed in said patent, there are three types of optical isomers of trehalose, i.e., $\alpha$, $\alpha$-trehalose, $\alpha$, $\beta$-trehalose and $\beta$, $\beta$-trehalose. All isomers exert therapeutic and/or prophylactic effect on signs of Sjorgen syndrome.

U.S. Pat. No. 6,723,170 discloses a crystalline trehalose dihydrate with low hydroscopicity. Variety of uses are disclosed for the crystalline trehalose dihydrate, including its use as a sweetener, taste-improving agent, in feeds and pet foods for animals, in soaps, skin creams, body shampoos, hair creams, moisture-controlling agent and a host of other uses disclosed in said patent.

Notwithstanding a variety of uses of trehalose disclosed in the prior art patents, none of them recognize the efficacy of trehalose for use in topical drying composition. In a commonly assigned, copending application Ser. No. 12/214,863 filed Jun. 24, 2008, there is described a topical drying composition containing an effective amount of trehalose, in hydrous or anhydrous form. The composition described therein, whether in aqueous solution form or a cream, when applied to the area of the skin which is vulnerable to perspiration, was effective in drying the perspiration resulting from aerobic or other vigorous sweat-producing exercises. The aforementioned copending application discloses several trehalose-containing formulations which are effective topical drying compositions. Neither of the prior art patents, nor the aforementioned patent application disclose the use of encapsulated trehalose in formulations used for topical drying compositions and sweat removal.

Therefore, it is an object of the present invention to use encapsulated trehalose in topical drying compositions.

It is a further object of the present invention to provide a more effective drying composition which includes encapsulated trehalose as the effective ingredient for sweat removal.

It is another object of the present invention to provide a topical drying composition which contains encapsulated trehalose and known aluminum compounds used in lesser quantities than have heretofore been used in the prior art sweat removing drying compositions using only known aluminum compounds.

It is also an object of the present invention to provide a method of using these compositions for topical drying and sweat removal.

The foregoing and other objects and advantages of the present invention will be appreciated from the ensuing detailed description and the illustrative examples.

SUMMARY OF THE INVENTION

A topical drying composition is provided for removal of sweat from the skin in areas which are vulnerable to sweating after sweat producing exercises such as playing tennis, golf, running, basketball, etc. The composition of this invention comprises, as its effective component, encapsulated trehalose wherein trehalose particles are encapsulated in a suitable medium such as a solution of dimethicone 200. A suitable effective composition comprises the following ingredients: trehalose, dimethicone, distilled water, Carbopol Ultrex 10, tetra sodium ethylene diamine tetra acetic acid, sorbitan monolaurate, cocoa butter, polysorbate 20 (Tween 20), Germal II (antibacterial agent), hyamine, bovine collagen (2% aqueous), elastin 2% aqueous (natural) and 10% sodium hydroxide to a pH of 6.4.

Another suitable composition which is effective for sweat removal includes aluminum zirconium compound which contains far less aluminum than has heretofore been used in prior art compositions. The drastic reduction in the amount of aluminum is due to the use of encapsulated trehalose in the composition.

The application of an effective amount of composition containing encapsulated trehalose, with or without an aluminum compound, results in sweat removal from the skin. Volunteers applying an effective amount of the composition of this invention have experienced far less sweating after strenuous, normally sweat producing exercises.

DETAILED DESCRIPTION OF THE INVENTION

In accordance with this invention more effective sweat removal can be realized by using a composition which contains encapsulated trehalose as hereinafter described. The application of the composition of this invention to the sweating area of the skin effects removal of the sweat or perspiration in a controlled and longer acting manner due to controlled rate of release of trehalose.

In the following description, the invention will be described and its effectiveness will be shown by several examples which are intended to be illustrative but without limiting the invention. In order to prepare a composition which is useful for the purpose of this invention, the encapsulated trehalose is first prepared separately as described below, wherein all parts are by weight.

An aqueous alginate solution of 1% by weight concentration is prepared by dissolving 0.25 sodium alginate in 25 grams distilled water. Thereafter, 25 grams of trehalose (obtained from Sigma Aldrich, St. Louis, Mo.) was added to the sodium alginate solution and dissolved at 45° C. to form a 50% concentrated trehalose in the alginate solutions (solution A). Thereafter an aqueous calcium chloride solution was prepared by dissolving 0.5 gm of calcium chloride in 50 gms distilled water to form 1% weight solution (solution B). 25 grams of this calcium chloride solution was subjected to high shear mixing, at 1000 rpm, using a rotator type homogenizer (Fisher Powergen 125, Fisher Scientific, Pittsburgh, Pa.). 50 grams of solution A was added to solution B under the same high shear agitation to form a finely divided dispersed slurry of gelled particles of trehalose/calcium alginate in a continuous aqueous phase. 75 grams of this aqueous slurry is slowly added to 50 grams of silicone fluid, DC200, having a viscosity of 100 centistokes (Dow Corning, Midland, Mich.) under the same high shear agitation to form water-in-oil dispersion. The formation of the dispersion was facilitated by adding 3 grams of sorbitan monooleate (Cognis, Cincinnati, Ohio) into the silicone fluid prior to addition of the aqueous compound. The resulting dispersion was further dispersed in water and encapsulated as follows.

An aqueous solution of sodium carboxymethylcellulose CMC, Akucell AF 1703 (Akzo Nobel, Netherlands) was prepared by dissolving 0.2 gm of CMC in 106.8 grams of distilled water. To this CMC solution was added 2.5 grams of Tween 20, polyoxyethylene 20 sorbitan monolaurate (Croda, Edison, N.J.) and 2.5 grams of sorbitan monooleate and the solution was stirred in a magnetic stirrer at 500 rpm. Thereafter, the entire 128 gms of the trehalose/alginate/silicone dispersion is added to the CMC solution to form a dispersion of silicone phase wherein droplets of silicone oil contain dispersed particles of trehalose/alginate.

The resulting trehalose encapsulated composition is as follows:

| Component | Weight (g) | Weight % |
| --- | --- | --- |
| Sodium Alginate 1% soln | 25.0 | 10.00% |
| Trehalose | 25.0 | 10.00% |
| Calcium Chloride 1% soln | 25.0 | 10.00% |
| Dimethicone 200 | 50.0 | 20.00% |
| Span 80 | 5.5 | 2.20% |
| Sodium carboxymethylcellulose | 0.2 | 0.08% |
| Tween 20 | 2.5 | 1.00% |
| Cetrimonium chloride 1% soln | 10.0 | 4.00% |
| Water | 106.8 | 42.72% |
| Total | 250 | 100.00 |

Independently from preparation of the encapsulated trehalose, the following mixture was prepared and mixed with encapsulated trehalose.

450 grams of distilled water was charged to a reaction vessel equipped with a stirrer, at room temperature and combined pressure and 3.4 gram of Ultrex 10, a polyacrylic acid thickener, available from B.F. Goodrich Co., was added to the reaction vessel and mixed thoroughly with the water. Thereafter, 2 grams of tetra sodium ethylene diamine tetra acetic acid was added to the reaction vessel with continuous agitation. The result was a gel which was heated to 50° c.

Another mixture was also prepared containing 38 gm sorbitan monolaureate and 11.4 grams of polysorbate 20 and 31 grams cocoa butter, and the mixture heated to 50° c. with continuous agitation.

The above two mixtures were then combined slowly forming a creamy homogenous mixture and cooled to room temperature. The creamy mixture had the following composition:

| Ingredients | Weight gm | Weight % |
| --- | --- | --- |
| Distilled water | 450 | 84 |
| Carbapol Ultrex 10 [1] | 3.4 | 0.63 |
| Tetra Sodium (DETA) | 2.0 | .37 |
| Cocoa butter | 31 | 5.78 |
| Sorbitan monolaurate | 38 | 7.09 |
| Polysorbate 20 (Tween 20) | 11.4 | 2.13 |
| TOTAL WEIGHT | 535.8 | 100.00 |

[1] carboxy polymethylene

The encapsulated composition which was formed as previously described was the then mixed with the above creamy composition. The final encapsulated formula has the following composition.

| Ingredients | Weight % |
| --- | --- |
| Trehalose | 3.30 |
| Dimethicone | 6.60 |
| Distilled water | 79.36 |
| Carbopol Ultrex 10 | .20 |
| Tetra sodium ethylene diamine tetra acetic acid | .13 |
| Sorbitan monolaurate | 2.50 |
| Cocoa butter | 2.00 |
| Polysorbate 20 (Tween 20) | .76 |
| Germal II (antibacterial agent) | .15 |
| Hyamine | 2.10 |
| Bovine collagen 2% aqueous | 2.00 |
| Elastin 2% acqueous (natural) | 1.00 |
| 10% sodium hydroxide to a pH of 6.4 | |
| TOTAL | 100 |

Clinical Test

The encapsulated formula hereinbefore described was tested for its sweat removal efficacy. Three males and three female volunteers were tested. The ages and weight of the males and females are listed below.

All subjects cleaned their armpits thoroughly and then applied the composition as a cream to both armpits using their finger tips. Each volunteer was given six-one gram sample and instructed to apply the cream to the armpit and report the degree of sweating and odor after exercise.

| Males | Females |
| --- | --- |
| 1. Age 25, weight 165 lbs. | 1. Age 24, weight 110 lbs. |
| 2. Age 42, weight 185 lbs. | 2. Age 35, weight 125 lbs. |
| 3. Age 51, weight 250 lbs. | 3. Age 50, weight 150 lbs. |

Results in Males

1. No sweating or odor was reported by volunteer #1 after 2 hours of weight lifting followed by 15 minutes in a sauna 2. Insignificant sweating was observed after running for 5 miles in 70° F. weather.

3. Minimal sweating and odor were reported by volunteer #3 after three hours outdoors in hot, humid weather (85° F.).

Results in Females

1. Minimal sweating but some odor was reported after running 3 miles on a treadmill.

2. Some sweating was reported with no odor after performing strenuous aerobic exercise for 45 minutes. Minimal sweating and odor on second day.

3. No sweating was observed after working from 9:00 A.M. to 5:00 PM, and no tackiness reported.

In another embodiment of this invention aluminum may be added to the encapsulated formulation hereinbefore described. The aluminum is added as aluminum compound or aluminum-zirconium compound such as, for example, aluminum chlorohydrate, aluminum chlorohydrex polyethylene glycol, aluminum chlorohydrex propylene glycol, aluminum dichlorohydrate, aluminum dichlorohydrex polyethylene glycol, aluminum dichlorohydrex propylene glycol, aluminum sesquichlorohydrate, aluminum sesquichlorohydrex polyethylene glycol, aluminum sesquichlorohydrex propylene glycol, aluminum zirconium octachlorohydrate, aluminum zirconium otachlorohydrex gly, aluminum zirconium pentachlorohydrate, aluminum zirconium pentachlorohydrex gly, aluminum zirconium tetrachlorohydrate, aluminum zirconium tetrachlorohydrex gly, aluminum zirconium trichlorohydrate, aluminum zirconium trichlorohydrex gly, buffered aluminum sulfate, potassium aluminum, sodium aluminum, chlorohydroxy lactate aluminum sesquichlorohydrates, sodium aluminum lactate, or mixtures thereof.

The use of small amounts of aluminum in the composition of this invention reduces the required quantity of trehalose without adversely affecting the sweat removal efficacy of the composition. The following examples describe the preparation of such aluminum-containing compositions, these examples are intended to be illustrative without limiting the invention. The aluminum compound used in these examples was pharmaceutical grade aluminum zirconium tetrachlorohydrox gly.

Example 1

2.8 grams of the aluminum compound and 0.7 gm of hyamine were dissolved in distilled water and the solution was then combined with 121 gms of the encapsulated composition previously described, forming a homogenous cream. 20 percent sodium hydroxide solution was then added to the mixture to achieve a pH of 6.4. The resulting composition is set forth below:

| Ingredients | Wt. gm | Wt. % |
|---|---|---|
| Microencapsulated composition | 121.0 | 89.90 |
| Aluminum compound | 2.8 | 2.08 |
| Distilled water | 10.0 | 7.50 |
| Hyamine | 1.7 | 0.52 |
| 20% solution NaOH to pH 6.4 | | |
| | 134.5 | 100.00 |

The aluminum compound used in this example as well as in examples 2-5 was aluminum zirconian tetrachlorohydroxy gly having aluminum to zirconium ratio of about 3.40 to 3.80.

Following the same procedure in Example 1, four additional formulations were prepared having the following compositions:

Example 2

| Ingredients | Wt. gm | Wt. % |
|---|---|---|
| Microencapsulated composition | 100 | 82.64 |
| Aluminum compound | 4.6 | 3.80 |
| Distilled water | 14.2 | 11.75 |
| Hyamine | 2.21 | 1.81 |
| 20% solution NaOH to pH 6.4 | | |
| | 121 | 100.00 |

Example 3

| Ingredients | Wt. gm | Wt. % |
|---|---|---|
| Microencapsulated composition | 87.5 | 74.21 |
| Aluminum compound | 3.5 | 2.96 |
| Distilled water | 10 | 8.49 |
| Hyamine | 0.9 | .77 |
| Trehalose hydrous sigma corp | 16.0 | 13.57 |
| 20% solution NaOH to pH 6.4 | | |
| | 117.9 | 100.00 |

Example 4

| Ingredients | Wt. gm | Wt. % |
|---|---|---|
| Microencapsulated composition | 88 | 85.93 |
| Aluminum compound | 3.5 | 3.41 |
| Distilled water | 10 | 9.76 |
| Hyamine | 0.5 | .90 |
| 20% solution NaOH to pH 6.4 | | |
| | 102 | 100.00 |

Example 5

| Ingredients | Wt. gm | Wt. % |
|---|---|---|
| Microencapsulated composition | 121 | 89.83 |
| Aluminum compound | 2.8 | 2.08 |
| Distilled water | 10 | 7.42 |
| Hyamine | .9 | .67 |
| 20% solution NaOH to pH 6.4 | | |
| | 134.7 | 100.00 |

The foregoing compositions were tested clinically for their anti-sweating efficacy and the results are discussed below.

All volunteers were instructed not to use antiperspirants, deodorants or bath salts for (48) hours prior to the test. They were also instructed to wash their body clean by shower or bath. Each was instructed to apply by hand a generous amount of the composition to the normally sweaty skin area.

Results for example 1: Three male volunteers ages 25, 36 and 40 applied the compositions to each axilla of their armpit and to their forehead before exercising. After jogging for three miles each reported minimal sweating.

A second test was performed on these volunteers the next day in a sauna maintained at 100° F. and 60% humidity, for 15 minutes. At the end of the tests their entire body was covered with sweat but their armpits were dry.

Results of example 2: Four volunteers, three males, ages 29, 33 and 35 and one female age 35 were tested. The three males jogged for three miles and the female jogged for one mile. All had applied a generous amount of the composition to their underarms. No sweating was reported by any of the volunteers.

Clinical tests were also conducted on other volunteers using the compositions of the other examples with substantially the same results confirming either no sweating or minimal amount of sweating when applying the compositions to the normally sweaty area after exercise.

In the foregoing detailed description and the illustrative examples, the ingredients of the composition of this invention have been described with a certain degree to specificity, both as to the type of ingredients as well as the quantity of each ingredients. It is to be understood, however that the amount of said ingredient may vary within effective range, and the other known equivalent ingredients may be substituted for those specifically mentioned. Thus, when no aluminum compound is used, the amounts of the different ingredients can vary as set forth below, all percentages being on weight basis.

| | |
|---|---|
| Trehalose | about 2 to about 4% |
| Dimethicone | about 1 to about 8% |
| Ultrex 10 | about 1 to about 3% |
| Tetra sodium EDTA | about 1 to about 2% |
| Sorbitan monolaurate | about 2 to about 3% |
| Cocoa butter | about 1.2 to about 2.5% |
| Polysorbate 20 | about 0.6 to about 0.9% |
| Germal | about 0.1 to about 3% |
| Hyamine | about 1 to about 3% |
| Bovine Collagen 2% aqueous | about 1 to about 3% |
| Elastin 2% aqueous | about 0.5 to about 4% |
| Distilled water | sufficient to 100% |

Add 10% to NaOH solution to pH of about 6-7, preferably about 6.4

When using aluminum-zirconium compound in the composition, the amount of this compound may vary from about 1 to about 4 weight percent of the composition.

As it was previously mentioned the encapsulated trehalose is formed separately and thereafter mixed with the remaining ingredients. Instead of sodium alginate, other soluble salts of alginate may be used such as, e.g., potassium or amonium alginate. Also, instead of calcium chloride, other water soluble calcium salts can be used.

Other ingredients of the composition may vary. For example, instead of sorbitan monolaurate be substituted by sorbitan monopalmitate, sorbitan monostearate, sorbitan tristearate, sorbitan monooleate, sorbitan sesquioleate, sorbitan trioleate; cocoa butter may be substituted by cocoa powder, olive oil, beeswax, having aloe; bovine collagen may be substituted by marine collagen or ATP (adenine triphosphate, disodium EDTA and trisodium EDTA may be used in lieu of tetra sodium EDTA; and the following may be substituted for carbopol ultrex 10 thickener; non benzene carbopol polymer such as carbopol 5984 and ultrex 10 NF polymers, carbopol 974P NF polymer, carbopol 980 NF and ultrex 10 NF polymers, carbopol 71G NF, 971P NF and 981 NF polymers, pemulen TR-1 and TR-2 NF polymers or benzene grade carbopol polymers such as carbopol 934 NF polymer, carbopol 934P NF polymer, carbopol 940 NF polymer, carbopol 941 NF polymer, carbopol 1342 NF polymer.

Substitution of different ingredients for those specified in the foregoing composition are generally known to those skilled in the art from the detailed description.

The invention claimed is:

1. A topical drying composition consisting essentially of:
   (a) an effective amount of trehalose in the form of trehalose-containing gelled calcium alginate particles dispersed within droplets of silicone oil in which said trehalose-containing calcium alginate particles are encapsulated and contained within said droplets of silicone oil, and wherein said droplets of silicone oil are themselves dispersed within an aqueous phase external to said droplets of silicone oil,
   (b) from about 1 to about 5 weight percent of sorbitan monolaurate,
   (c) from about 0.5 to about 2.5 weight percent polysorbate 20,
   (d) from about 1 to about 3 weight percent benzethonium chloride,
   (e) an acceptable carrier for said composition, and
   (f) a pH adjuster to adjust the pH of said composition between about 5.5 to about 7.0.

2. A topical drying composition as in claim 1 wherein the pH of said composition is between about 6.0 and about 6.6.

3. A topical drying composition as in claim 1 wherein said carrier is sterilized water.

4. A topical drying composition as in claim 2 wherein said carrier is distilled water.

5. A topical drying composition as in claim 1 further including from about 0.1 to about 4.0 weight percent carboxy polymethylene and from about 0.1 to about 0.6 weight percent tetra sodium ethylene diamine tetra acetic acid.

6. A topical drying composition as in claim 2 further including from about 0.1 to about 4.0 weight percent carboxy polymethylene and from about 0.1 to about 0.6 weight percent tetra sodium ethylene diamine tetra acetic acid.

7. A topical drying composition as in claim 3 further including from about 0.1 to about 4.0 weight percent carboxy polymethylene and from about 0.1 to about 0.6 weight percent tetra sodium ethylene diamine tetra acetic acid.

8. A topical drying composition as in claim 4 further including from about 0.1 to about 4.0 weight percent carboxy polymethylene and from about 0.1 to about 0.6 weight percent tetra sodium ethylene diamine tetra acetic acid.

9. A topical composition as in claim 1 further including an aluminum-zirconium compound wherein the ratio of aluminum to zirconium is from about 3.4 to about 3.8, and the amount of aluminum in the composition is from about 1 to about 10 weight percent.

10. A topical composition as in claim 2 further including an aluminum-zirconium compound wherein the ratio of aluminum to zirconium is from about 3.4 to about 3.8, and the amount of aluminum in the composition is from about 1 to about 10 weight percent.

11. A topical composition as in claim 3 further including an aluminum-zirconium compound wherein the ratio of aluminum to zirconium is from about 3.4 to about 3.8, and the amount of aluminum in the composition is from about 1 to about 10 weight percent.

12. A topical composition as in claim 4 further including an aluminum-zirconium compound wherein the ratio of aluminum to zirconium is from about 3.4 to about 3.8, and the amount of aluminum in the composition is from about 1 to about 10 weight percent.

13. A topical composition as in claim 2 further including an aluminum-zirconium compound wherein the ratio of aluminum to zirconium is from about 3.4 to about 3.8, and the amount of aluminum in the composition is from about 1 to about 10 weight percent.

14. A topical composition as in claim 6 further including an aluminum-zirconium compound wherein the ratio of aluminum to zirconium is from about 3.4 to about 3.8, and the amount of aluminum in the composition is from about 1 to about 10 weight percent.

15. A topical composition as in claim 7 further including an aluminum-zirconium compound wherein the ratio of aluminum to zirconium is from about 3.4 to about 3.8, and the amount of aluminum in the composition is from about 1 to about 10 weight percent.

16. A topical composition as in claim 2 further including an aluminum-zirconium compound wherein the ratio of aluminum to zirconium is from about 3.4 to about 3.8, and the amount of aluminum in the composition is from about 1 to about 10 weight percent.

17. A method of absorbing perspiration, the method comprising applying the topical drying composition of claim 1 to a surface of a user's skin, wherein perspiration emitted thereafter through the surface of the user's skin is absorbed by the topical drying composition.

\* \* \* \* \*